United States Patent [19]

Beck et al.

[11] Patent Number: 5,173,498

[45] Date of Patent: Dec. 22, 1992

[54] SUBSTITUTED 3-THIA- AND 3-OXA-ALKYLFLAVONES, A PROCESS FOR THEIR PREPARATION, THE USE THEREOF, MEDICAMENTS BASED ON THESE COMPOUNDS AND INTERMEDIATES

[75] Inventors: Gerhard Beck, Frankfurt am Main; Ulrich Schacht, Hofheim am Taunus; Kurt Kebeler, Bad Soden am Taunus; Ernold Granzer, Kelkheim/Taunus, all of Fed. Rep. of Germany

[73] Assignee: Hoechst Aktiengesellschaft, Frankfurt am Main, Fed. Rep. of Germany

[21] Appl. No.: 680,255

[22] Filed: Apr. 4, 1991

[30] Foreign Application Priority Data

Apr. 6, 1990 [DE] Fed. Rep. of Germany ....... 4011187

[51] Int. Cl.$^5$ .................... A61K 31/35; C07D 311/30
[52] U.S. Cl. ..................................... 514/456; 549/403
[58] Field of Search ......................... 549/403; 514/456

[56] References Cited

U.S. PATENT DOCUMENTS

| 3,462,455 | 8/1969 | Kramer et al. | 549/403 |
| 4,591,600 | 5/1986 | Creuzet et al. | 514/456 |
| 4,713,465 | 12/1987 | Kramer et al. | 549/403 |
| 4,788,215 | 11/1988 | Kramer et al. | 514/456 |
| 4,925,852 | 5/1990 | Kesseler et al. | 514/333 |

FOREIGN PATENT DOCUMENTS

| 121489 | 10/1984 | European Pat. Off. . |
| 122053 | 10/1984 | European Pat. Off. . |
| 183169 | 6/1986 | European Pat. Off. . |
| 6009 | 5/1968 | France . |

OTHER PUBLICATIONS

Beck et al., Tetrahedron Lett., 1990, 31(50), 7293-6. (CA 114:101,427x, 1991).
Monty Krieger et al., "Replacement of Neutral Lipids of Low Density Lipoprotein with Esters of Long Chain Unsaturated Fatty Acids", *The Journal of Biological Chemistry*, vol. 254, No. 10, Issue of May 25, pp. 3845-3853, 1979.
Hermann Esterbauer et al., "Autoxidation of Human Low Density Lipoprotein Loss of Polyunsaturated Fatty Acids and Vitamin E and Generation of Aldehydes", Journal of Lipid Research, vol. 28, 1987, pp. 495-508.
Toru Kita et al., "Probucol Prevents the Progression of Atherosclerosis in Watanabe Heritable Hyperlipidemic Rabbit, an Animal Model for Familial Hypercholesterolemia", Proc. Natl. Acad. Sci. USA, vol. 84, pp. 5928-5931, Aug. 1987.
Wulf Palinski et al., "Low Density Lipoprotein Undergoes Oxidative Modification in Vivo", *Proc. Natl. Acad. Sci. USA*, vol. 86, pp. 1372-1376, Feb. 1989.

Primary Examiner—Nicky Chan
Attorney, Agent, or Firm—Finnegan, Henderson, Farabow, Garrett and Dunner

[57] ABSTRACT

Substituted 3-thia- and 3-oxa-alkylflavones of formula I

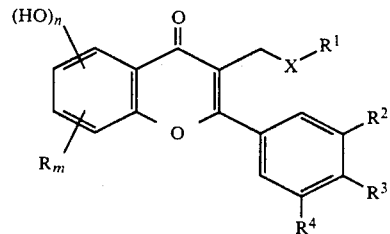

wherein R, $R^1$, $R^2$, $R^3$, $R^4$, X, m and n have the indicated meanings, a process for the preparation of these compounds and their use as medicaments and pharmaceutical preparations are described. In addition, new intermediates for the preparation of the compounds of formula I are described.

5 Claims, No Drawings

SUBSTITUTED 3-THIA- AND 3-OXA-ALKYLFLAVONES, A PROCESS FOR THEIR PREPARATION, THE USE THEREOF, MEDICAMENTS BASED ON THESE COMPOUNDS AND INTERMEDIATES

DESCRIPTION

Epidemiological studies in many countries over the past three decades indicate a dependence between raised cholesterol concentrations in the blood and the risk of cardiac infarction (e.g. The Framingham Study, Ann. Intern. Med. 74 (1971) 1-12). In particular, raised low density lipoprotein (LDL) levels in the plasma are considered to be responsible for this. Studies in recent years (W. Palinski et al., Proc. Natl. Acad. Sci. USA 86, 1372 (1989), ibid. 84, 2995 (1987) and Kita et al., ibid 84, 5928 (1987)) have shown that oxidative modification of the LDL particles by free radicals such as, for example, .OH, $O_2^-$ or by singlet oxygen is responsible for their atherogenic action. The oxidation of LDL is initiated by the oxidation of the polyunsaturated fatty acids in the LDL particle. The degradation products of lipid peroxidation are reactive aldehydes, such as, for example, nonenal or malonic dialdehyde, which react with lysine residues of the LDL binding protein Apo B (Esterbauer et al., J. Lipid. Res. 28, 495 (1987)). The chemically modified LDL particles are then absorbed in an uncontrolled manner via so-called scavenger receptors by macrophages and convert the latter into foam cells, which manifest themselves as arteriosclerotic lesions. The compounds comprised by the present application are LDL-specific antioxidants which prevent the oxidation of the LDL particles. The specificity of the compounds is achieved by linking flavones having an antioxidant action with branched or non-branched lipophilic residues, which are preferably incorporated in LDL particles (cf. M. Krieger, M. J. MC Phaul, J. L. Goldstein, M. S. Brown, J. Biol. Chem 254, 3845 (1979)).

The present invention relates to flavones of formula I

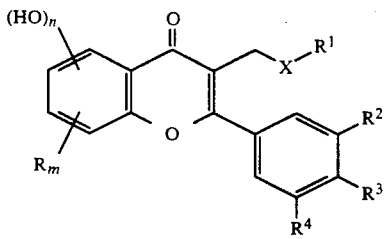

in which:
X is sulfur or oxygen,
R is halogen, $C_1$-$C_4$)-alkyl or trifluoromethyl,
m is 0, 1, 2 or 3,
n is 1 or, if m=0, 1 or 2, also 2,
$R^1$ is ($C_1$-$C_{25}$)-alkyl or ($C_3$-$C_{25}$)-alkenyl, one $CH_2$ group optionally being replaced by oxygen, or is ($C_3$-$C_{25}$)-alkenyl, which is substituted by cyclohexenyl, which in turn contains 1-3 methyl groups, and
$R^2$, $R^3$ and $R^4$ are hydrogen, hydroxyl, halogen, ($C_1$-$C_4$)-alkyl, ($C_1$-$C_4$)-alkoxy or trifluoromethyl, $R^2$, $R^3$ and $R^4$ being identical or different.

If m is 2 or 3, the radicals R are identical or different.

In the foregoing and following statements, alkyl, alkenyl and alkoxy are always straight-chain or branched radicals and halogen is fluorine, chlorine or bromine.

Insofar as the radicals $R^1$ contain one or more centers of asymmetry, the pure enantiomers, diastereomers and racemates are included. For $R^1$=($C_3$-$C_{25}$)-alkenyl, the possible E and Z isomers are also claimed. The alkylene radicals are preferably mono-unsaturated to hexa-unsaturated.

Amongst the substituents, the following are preferred:
X sulfur or oxygen
R fluorine, chlorine, ($C_1$-$C_3$)-alkyl or trifluoromethyl,
m 0, 1, 2 or 3,
n 1 or, if m is 0, 1 or 2, also 2,
$R^1$ ($C_4$-$C_{22}$)-alkyl or ($C_4$-$C_{25}$)-alkenyl, it being possible for one $CH_2$ group optionally to be replaced by oxygen, and
$R^2$, $R^3$ and $R^4$ hydrogen, hydroxyl, fluorine, chlorine, ($C_1$-$C_3$)-alkyl, ($C_1$-$C_3$)-alkoxy or trifluoromethyl, $R^2$, $R^3$ and $R^4$ being identical or different.

Amongst the substituents, the following are particularly preferred:
X sulfur,
R fluorine, chlorine, methyl or trifluoromethyl,
m 0, 1, 2 or 3,
n 1 or, if m is 0, 1 or 2, also 2,
$R^1$ ($C_4$-$C_{22}$)-alkyl or ($C_4$-$C_{22}$)-alkenyl, it being possible for one $CH_2$ group optionally to be replaced by oxygen, and
$R^2$, $R^3$ and $R^4$ hydrogen, hydroxyl, fluorine, chlorine, methyl, methoxy or trifluoromethyl, $R^2$, $R^3$ and $R^4$ being identical or different.

The invention also relates to a process for the preparation of the compounds of formula I, which comprises a converting a phenol of formula II

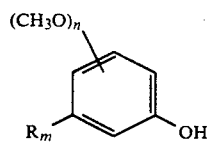

wherein m, n and R have the meaning indicated for formula I, by acylation into the compounds of formula III

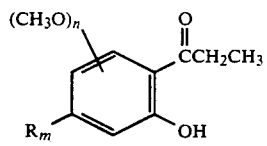

wherein m, n and R have the meaning indicated for formula I, b) acylating a compound of formula III on the free phenolic hydroxyl group using an acid halide of formula IV

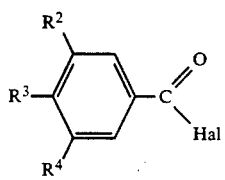

wherein $R^2$, $R^3$ and $R^4$ have the meaning indicated for formula I and Hal is bromine or chlorine, to give a compound of formula V

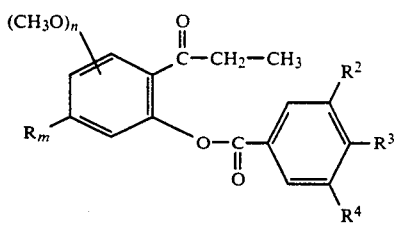

V wherein m, n, R and $R^2$, $R^3$ and $R^4$ have the meaning indicated for formula I,
cyclizing a compound of formula V to give a compound of formula VI

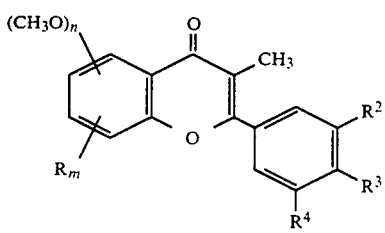

VI wherein m, n, R and $R^2$, $R^3$ and $R^4$ have the meaning indicated for formula I,
d) splitting off the methoxy groups from a compound of formula VI, to give a compound of formula VII

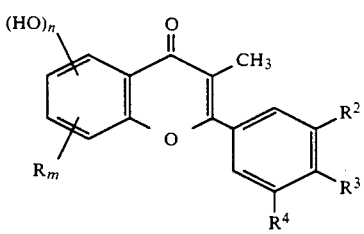

VII wherein m, n and R as well as $R^2$, $R^3$ and $R^4$ have the meaning indicated for formula I,
e) reacting a compound of formula VII with an acylating agent to give a compound of formula VIII

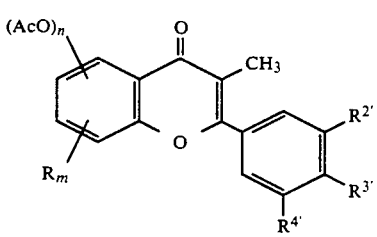

VIII wherein m, n and R have the meaning indicated for formula I and $R^{2'}$, $R^{3'}$ and $R^{4'}$ are hydrogen, halogen, ($C_1$-$C_4$)-alkyl, ($C_1$-$C_4$)-alkoxy, trifluoromethyl or acyloxy, $R^{2'}$, $R^{3'}$ and $R^{4'}$ being identical or different,
f) selectively halogenating a compound of formula VIII to give a compound of formula IX

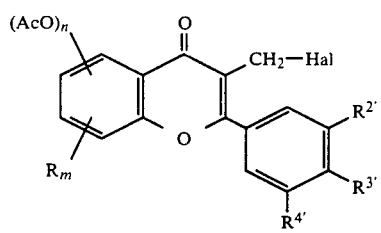

IX wherein m, n and R have the meaning indicated for formula I, $R^{2'}$, $R^{3'}$ and $R^{4'}$ have the meaning indicated for formula VIII and Hal is chlorine, bromine or iodine,
g) reacting a compound of formula IX with a compound of formula X

X wherein X and R have the meaning indicated for formula I, to give a compound of formula XI

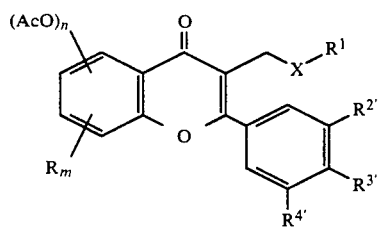

XI wherein m, n, X, R and $R^1$ have the meaning indicated for formula I and $R^{2'}$, $R^{3'}$ and $R^{4'}$ have the meaning indicated for formula VIII, and
h) splitting off the acyl protective groups from a compound of formula XI to give a compound of formula I.

The phenols of formula II, which are used as starting materials in the process according to the invention, are obtainable commercially (e.g. Fluka, Aldrich) or can be prepared by processes disclosed in the literature (e.g. R. O. Duthaler, Helv. Chim. Acta 67. 1411 (1984) or M. V. Sargent et al., J. Chem. Soc. 1974, p. 1353)).

To prepare the substituted propiophenones III, the phenols of formula II are acylated by a Friedel-Crafts reaction, for example with propionyl chloride in the presence of $AlCl_3$ or $BF_3$ etherate; however, a preferred embodiment comprises carrying out the reaction analogously to the process which has been described by Canter, F. W. et al., J. Chem. Soc. 1 (1931) 1245. The subsequent O-acylation of the propiophenones III is carried out using the acid halides of formula IV, appropriately in a solvent such as tetrahydrofuran, acetone, DMF or dimethyl sulfoxide, in the presence of a suitable base, such as, for example, triethylamine, $K_2CO_3$, sodium hydride, potassium tert-butylate, sodium ethylate or butyllithium, at temperatures of $-20°$ C. to $+50°$ C. for a period of 1-6 hours.

The acid chlorides IV are obtainable commercially or can be prepared by processes disclosed in the literature (Organikum, Verlag VEB, p. 387-88, 4th edition 1964, Berlin).

The O-acylated propiophenones of formula V are cyclized, for example, in a solvent such as dimethylformamide or dimethyl sulfoxide in the presence of sodium hydride or Na-ethylate at temperatures of −25° C. to +80° C. for a period of 1–8 hours.

The methoxy protective groups are removed from the cyclized compounds of formula VI by ether-splitting. This can be effected, for example, by treatment in methylene chloride or chloroform in the presence of boron tri-bromide at −10° C. to +30° C. over a period of 1–4 hours. The methoxy groups can also be split off by warming with hydriodic acid (48%) or concentrated hydrobromic acid (48%). In general, only the methoxy groups present in the benzopyrone radical are split off at −10° C. to +25° C., whereas temperatures of +40° C. to +110° C. are necessary for splitting off methoxy groups (for example $R^2$, $R^3$ or $R^4$) in the phenyl radical in the 2-position.

The free hydroxyl groups in the compounds of formula VII are protected by acylation. Suitable acylating agents are aliphatic or aromatic acid halides or acid anhydrides. The acylation is preferably carried out in solvents such as methylene chloride, chloroform or toluene, at temperatures between 0° C. and +40° C., in the presence of bases, such as, for example, triethylamine, pyridine etc. The preferred embodiment, however, comprises acylation in pyridine with acetic anhydride at temperatures of +30° C. to +90° C. within a period of ½–2 hours.

The acylated compounds of formula VIII are selectively halogenated at the 3-$CH_3$ group. Halogenating agents which can be used are N-Hal-succinimides (Hal=Cl, Br or I) or elemental chlorine or bromine in the presence of compounds which form free radicals, such as, for example, azoisobutyronitrile or benzoyl peroxide, or under irradiation with UV light. The bromination is effected particularly simply by warming the compounds VIII in carbon tetrachloride in the presence of N-bromo-succinimide at 0°–50° C. with simultaneous irradiation with UV light.

The reaction of the halides of formula IX with the alcohols or mercaptans of formula X to give the compounds of formula XI is carried out, for example, at −30° C. to +60° C. in solvents such as tetrahydrofuran, DME, diethyl ether, DMF or dimethyl sulfoxide, in the presence of 1 eq. of base, such as, for example, sodium hydride, butyl-lithium, triethylamine or sodium ethylate. The straight-chain alcohols of formula X ($R^1$-OH) are available commercially or can be prepared in accordance with generally known methods (e.g. Organikum, Verlag VEB Berlin 1964, Methodenregister p. 4, Alkohole). The branched alcohols, such as, for example, geraniol, nerol, farnesol and phytol, are also available commercially (Aldrich Chemie, Steinheim) or are prepared by the method described by J. W. K. Burrell, J. Chem. Soc. (C) 1966, p. 2144–2154. The mercaptans of formula X ($R^1$-S-H) are prepared from the corresponding alcohols by conversion to the bromides using phosphorus tribromide (e.g. 0. Isler et al., Helv. Chim. Acta 108, p. 903 (1956)) and reaction of the bromides with thiourea with subsequent alkaline hydrolysis of the S-alkyl thiuronium salts, analogously to the method described, for example, in Organikum, Verlag VEB, Berlin 1964, p. 176. The mercaptans can also be prepared directly, as described by R.P. Valante in Tetrahedron Letters 22, 3119 (1981), from the corresponding alcohols.

In order to prepare the compounds, according to the invention, of formula I, the acyl protective groups are split off from the compounds of formula XI. For this purpose the compounds XI are preferably dissolved in solvents, such as, for example, alcohols, DME/$H_2O$ or dipolar aprotic solvents, such as DMF, acetonitrile and DMSO, and treated with several equivalents of $K_2CO_3$ or NaOH and saponified at temperatures of 0° C. to +40° C. for 1–2 hours. A preferred embodiment comprises dissolving in methanol or ethanol and treating with 2–4 equivalents of potassium carbonate at room temperature for 2 hours.

Insofar as the individual reaction products are not already obtained in sufficiently pure form, so that they can be employed for the subsequent reaction step, a purification by means of crystallization, column chromatography, thin layer chromatography or high pressure liquid chromatography is advisable.

In addition to the compounds described in the examples, the following compounds can be prepared by the process according to the invention:

2-(4',5'-dihydroxyphenyl)-3-(2-thia-octadec-1-yl)-5,7-dihydroxy-4-H-benzopyran-4-one 2-(4',5'-dihydroxyphenyl)-3-(2-thia-5,9R,13R,17-tetramethyl-4E-octadecen-1-yl)-5,7-dihydroxy-4-H-benzopyran-4-one 2-(4',5'-dihydroxyphenyl)-3-(2-thia-5,9,13-trimethyl-4E,8E,12E-tetradecatrien-1-yl)-5,7-dihydroxy- 4-H-benzopyran-4-one 2-(4',5'-dihydroxyphenyl)-3-(2-thia-10-oxa-5,9,9-trimethyl-4Z-dodecen-1-yl)-5,7-dihydroxy-4-H-benzopyran-4-one 2-(4',5'-dihydroxyphenyl) 3-(2-thia-5,9-dimethyl-4E,8E-decen-1-yl)-5,7-dihydroxy-4-H-benzopyran-4-one 2-(4',5'-dihydroxyp-henyl)-3-(2-thia-5,9-dimethyl-11-(2,6,6-trimethyl-1-cyclohexenyl)-4E,6E,8E,10E-undecen-1-yl)-5,7-dihydroxy-4-H-benzopyran-4-one 2-(4',5'-dihydroxyphenyl)-3-(2-thia-eicosan-1-yl)-6,8-dihydroxy-4-H-benzopyran-4-one 2-(4',5'-dihydroxyphenyl)-3-(2-thia-eicosan-1-yl)-6-hydroxy-4-H-benzopyran-4-one 2-(4'-chlorophenyl)-3-(2-thia-octadec-1-yl)-6-hydroxy-4-H-benzopyran-4-one 2-(4'-fluorophenyl)-3-(2-thia-5,9R,13R,17-tetramethyl-4E-octadecen-1-yl)-6,8-dihydroxy-4-H-1-benzopyran-4-one 2-(4'-fluorophenyl)-3-(2-thia-5,9R,13R,17-tetramethyl-4E-octadecen-1-yl)-6-hydroxy-4H-1-benzopyran-4-one 2-(4',5'-dihydroxyphenyl)-3-(2-thia-5,9R,13R,17-tetramethyl-4E-octadecen-1-yl)-6,8-dihydroxy-4H-benzopyran-4-one 2-(4'-fluorophenyl)-3-(2-thia-5,9R,13R,17-tetramethyl-4E-octadecen-1-yl)-7,8-dihydroxy-4H-benzopyran-4-one 2-(4'-methoxyphenyl)-3-(2-thia-5,9R,13R,17-tetramethyl-4E-octadecen-1-yl)-6,8-dihydroxy-4H-benzopyran-4-one 2-(4'-hydroxyphenyl)-3-(2-thia-5,9-dimethyl-11-(2,6,6-trimethyl-1-cyclohexenyl)-4E,6E,8E,10E-undecen-1-yl)-5,7-dihydroxy-4H-benzopyran-4-one 2(4'-methoxyphenyl)-3-(2-thia-5,9,13-trimethyl-4E,8E,12E-tetradecatrien-1-yl)-5,7-dihydroxy-4H-benzopyran-4-one 2-(4'-methoxyphenyl-3-(2-thia-octadec-1-yl)-5,7-dihydroxy-4-benzopyran-4-one 2-(4'-chlorophenyl)-3-(2-thia-5,9R,13R,17-tetramethyl-4E-octadecen-1-yl)-6,8-dihydroxy-4H-benzopyran-4-one 2-(4',5'-dihydroxyphenyl)-3-(2-thia-5,9R,13R,17-tetramethyl-4E-octadecen-1-yl)-7,8-dihydroxy-4H-benzopyran-4-one 2-(4'-fluorophenyl)-3-(2-oxa-5,9R,13R,17-tetramethyl-4E-octadecen-1-yl)-5,6-dihyiroxy-4H-benzopyran-4-one 2-(4'-fluorophenyl)-3-(2-oxa-5,9-dimethyl-11-(2,6,6-trimethyl-1-cyclohexenyl)-4E,6E,8E,10E-undecen-1-yl)-5,7-dihydroxy-4H-benzopyran-4-one 2-(4'-fluorophenyl)-3-(2-oxa-octadec-1-yl)-5,7-dihydroxy-4H-benzopyran-4-one 2-(4'-fluorophenyl)-3-(2-thia-5,9,13,17-tetramethyl-octadecan-1-yl)-5,7-dihydroxy-4H-benzopyran-4-one 2-(4,-fluorophenyl)-3-(2-oxa-5,9,13,17-tetramethyl-octadecan-1-yl)-5,7-dihydroxy-4H-benzopyran-4-one Biological test systems 1. Inhibition of LDL oxidation The method for testing the antioxidant action of the substances is based on the inhibition of the $Cu^{2+}$-catalyzed oxidation of LDL by active compounds, the increase in fluorescence at 430 nm serving as a measure of the LDL oxidation (U.P. Steinbrecher, J. Biol. Chem. 262. 3603 (1987)).

Blood from freshly slaughtered pigs, which was collected in the presence of EDTA (1 mg/ml) and $NaN_3$ (0.1 mg/ml) and then centrifuged for 20 min at $2,000 \times g$ and 4° C. in order to remove the cellular constituents, was used for isolation of the LDL. Stepwise ultracentrifuging of the plasma in NaCl/NaBr solutions having densities of $d = 1.019$ and $d = 1.063$ yielded the LDL fraction (R. J. Havel, H. A. Eder and J. H. Bragdon, J. Clin. Investig. 34, 1345 (1955)). In this method the samples were centrifuged in a 50.2 Ti fixed angle rotor (Beckman Instruments) in each case for 18 hours at $300,000 \times g$ and 17° C. In order to lower the EDTA concentration, the LDL fraction obtained in this way had to be subjected for 48 hours to two dialyses in 100 times the volume of a phosphate-buffered saline solution (160 mM NaCl, 10 mM $NaH_2PO_4$) of pH 7.4 (U. P. Steinbrecher, J. L. Witztum, S. Parthasarathy and D. Steinberg, Arteriosclerosis 7, 135 (1987)). The subsequent purity check on the LDL fraction by agarose gel electrophoresis (U. P. Steinbrecher, J. L. Witztum, S. Parthasarathy and D. Steinberg, Arteriosclerosis 7, 135 (1987)) showed a single band.

For the oxidation tests, the LDL fraction, which was stored at 4° C., was diluted to 0.1 mg of protein/ml using the dialysis buffer of the abovementioned composition. 2.5 ml of this LDL solution were treated with 25 µl of ethanolic solution having various concentrations of the test substance and the samples were incubated in closed vessels under nitrogen for 1 hour at 37° C., in order initially to achieve an adequate incorporation of the substance in the LDL particles (L. R. McLean and K. A. Hagaman, Biochemistry 28, 321 (1989)). The maximum concentration of the test compounds was 10 µM in the test.

The oxidation of the LDL was effected by adding 12.5 µl of a 1 mM $CuSO_4$ solution, i.e. 5 µM $Cu^{2+}$ in the test, and incubating for two hours at 37° C. in cell culture dishes open to the air. The controls contained 25 µl of pure ethanol. To determine the blank, analogously prepared LDL samples were treated with 12.5 µl of a solution of 1 mM $CuSO_4$ and 40 mM EDTA and likewise incubated for 2 hours at 37° C.

After the end of the incubation, the fluorescence intensity emitted at 430 nm was determined in all samples using the excitation wavelength 365 nm (Perkin-Elmer type LS-3 spectrofluorimeter).

The $IC_{50}$ values, i.e. those molar concentrations which, under the test conditions described, inhibit the increase in fluorescence by 50% (controls = 100), were determined for comparison of the strength of action of the antioxidants. For this purpose the fluorescence measurement was carried out as a duplicate determination using, in each case, 5 to 6 different concentrations of the test substance. Plotting the percentage inhibition values on semi-logarithmic paper and graphic interpolation gave the corresponding $IC_{50}$ (Table I). Vitamin E was used as comparison compound.

TABLE I

| Compound according to Example | $IC_{50}$ mol/liter |
| --- | --- |
| 9b | $1.2 \times 10^{-5}$ |
| 9d | $8.0 \times 10^{-6}$ |
| 9e | $3.3 \times 10^{-7}$ |
| 9i | $9.0 \times 10^{-7}$ |
| Vitamin E | $4.8 \times 10^{-6}$ |

2. Suppression or inhibition of cholesterol biosynthesis in cell cultures of HEP-G2 cells Monolayers of HEP-G2 cells in lipoprotein-free nutrient medium were preincubated with corresponding concentrations of the test substances for a certain time (e.g. 1 hour) and after addition of the labeled precursor, for example $^{14}C$-sodium acetate, the incubation was continued (e.g. 3 hours). After addition of an internal standard ($^3H$-cholesterol), a portion of the cells was subjected to alkaline saponification. The lipids in the saponified cells were extracted with chloroform/methanol. After addition of carrier cholesterol, this lipid mixture was separated by preparative thin layer chromatography, the cholesterol band was isolated after rendering visible using iodine vapor and the amount of $^{14}C$-cholesterol formed from the $^{14}C$-precursor was determined by scintigraphy. Cell protein was determined in a aliquote portion of the cells, so that the amount of $^{14}C$-cholesterol formed per unit time per mg of cell protein can be calculated. By comparing this value with the amount of $^{14}C$-cholesterol which was formed per mg of cell protein and per unit time from a culture which was treated in the same way but free from test substance, the inhibitory effect of the particular test preparation on the cholesterol biosynthesis of HEP-G2 cell cultures was obtained.

Testing of substances for inhibition of cholesterol biosynthesis in confluent cell cultures (monolayer) of HEP-G2 cells

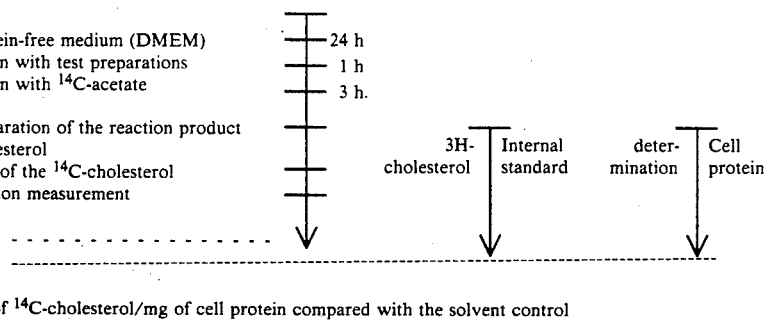

8. Result
  in nmol of $^{14}$C-cholesterol/mg of cell protein compared with the solvent control Using the method described above, for example, the following inhibitory values for the cholesterol biosynthesis (in HEP-G2 cells) were determined for the compounds according to the invention (the IC$_{50}$ value in mole/liter is that concentration of the compound which effects a 50% inhibition of the cholesterol biosynthesis) (Tab. II).

TABLE II

| Compound according to Example | IC$_{50}$ mol/liter |
|---|---|
| 9e | $1.0 \times 10^{-8}$ |
| 9i | $9.0 \times 10^{-9}$ |
| 9l | $8.0 \times 10^{-8}$ |
| 9m | $8.0 \times 10^{-8}$ |

The compounds of formula I are distinguished by substantial inhibition of the LDL oxidation and the cholesterol biosynthesis.

The compounds, according to the invention, of formula I are highly active antioxidants which prevent the LDL oxidation. Because of their specificity, they have a stronger action as endogenous antioxidants than, for example, vitamin E. The compounds are therefore suitable, as stated initially, for the prophylaxis and treatment of arteriosclerotic changes, such as, for example, coronary heart disease. They are also suitable for the treatment of other diseases in which free radicals are substantially involved, such as, for example, inflammations, rheumatism, cerebral infarction, cirrhosis of the liver, autoimmune diseases and cataract formation.

The compounds of formula I are, in addition, cholesterol biosynthesis inhibitors and as a result of this property contribute to a further lowering of the risk of arteriosclerosis.

High cholesterol levels are associated with a number of diseases, such as, for example, coronary heart disease or arteriosclerosis. Therefore, lowering of raised cholesterol levels for the prevention and treatment of such diseases is also a therapeutic aim.

The compounds of formula I are therefore suitable as antioxidants and hypolipidemic agents for the treatment and prophylaxis of arteriosclerotic changes.

The invention therefore also relates to pharmaceutical preparations based on these compounds and to their use as medicaments, in particular as antioxidants and hypolipidemic agents, and for the prophylaxis of arteriosclerotic changes.

The compounds of formula I are used as anti-arteriosclerotic agents, for example, in oral doses of 3 to 2,500 mg per day, but preferably in a dosage range of 10 to 500 mg. These daily doses can also be divided into two to four individual doses, as required, or can be administered in delayed release form. The dosage scheme can depend on the type, age, weight, sex and medical condition of the patient.

An additional cholesterol-lowering effect can be achieved by simultaneous administration of the compounds according to the invention with substances which bind bile acid, such as, for example, anion exchange resins. The excretion of bile acid leads to intensified new synthesis and thus to an increased degradation of cholesterol (cf. M. S. Brown, P. T. Koranen and J. C. Goldstein, Science 212, 628 (1981); M. S. Brown, J. C. Goldstein, Spektrum der Wissenschaft 1985, 1, 96).

The compounds, according to the invention, of formula I can be used as a solution or suspension in pharmacologically acceptable organic solvents, such as monohydric or polyhydric alcohols, such as, for example, ethanol, ethylene glycol or glycerol, in triacetin or in alcohol/acetaldehyde diacetal mixtures or oils, such as, for example, sunflower oil or cod-liver oil, ethers, such as, for example, diethylene glycol dimethyl ether, or also polyethers, such as, for example, polyethylene glycol, or also in the presence of other pharmacologically acceptable polymer excipients, such as, for example, polyvinylpyrrolidone, or in solid formulations.

For the compounds of formula I, solid formulations which can be administered orally and which may contain a customary adjuvant are preferred. They are prepared by conventional methods.

Suitable formulations for oral use are, in particular, tablets, coated tablets or capsules. One dosage unit preferably contains 10 to 500 mg of active substance.

The compounds of formula VIII, IX and XI are new and are valuable intermediates for the preparation of compounds of formula I. The invention therefore also relates to these compounds and to processes for their preparation.

Preliminary remark: Unless indicated otherwise, NMR spectra were measured in CDCl$_3$ using TMS as internal standard. The following abbreviations are used for the classification of NMR signals: s=singlet, d=doublet, p=pentet, t=triplet, q=quartet. Melting points are uncorrected.

General method for the preparation of compounds of formula I

Example 1a (m=0, n=2)

2-Hydroxy-4,6-dimethoxypropiophenone (IIIa)

Dry hydrogen chloride is passed into a mixture of 22.7 g of zinc chloride and 155 g (1.0 mol) of 3,5-dimethoxyphenol (IIa) (cf. Tab. 3) in 154 ml of freshly distilled propionitrile. The temperature rises to 80° C. After about 1 hour a further 50 ml of distilled propionitrile are added and hydrogen chloride is passed in for a further 4 hours, with stirring. The batch becomes crystalline overnight at room temperature. The imide chloride formed is treated with a mixture of 250 ml of water and 250 ml of ethanol and the mixture is heated for about 30 min at 80° C. until no further imide chloride is present in the thin layer chromatogram. On cooling in an ice bath, IIIa crystallizes out. The crystals are filtered off with suction and the mother liquor is concentrated to 1/3rd under vacuum and cooled again. The crystal fractions are combined and recrystallized from MeOH.

Yield: 142 g (67% of theory) of pale crystals, m.p. 113°–116° C. (IIIa) $R_f$ value=0.51 (cyclohexane/ethyl acetate=4:1)

Examples 1b–1e

Compounds IIIb–IIIe are prepared in a manner analogous to that described in Example 1a (cf. Tab. 2).

TABLE 1

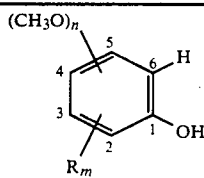

II

| Example | n | m | R | |
|---|---|---|---|---|
| a | 2 | 0 | — | 3,5-dimethoxyphenol (Aldrich,13,263-2) |
| b | 2 | 0 | — | 2,3-dimethoxyphenol (Aldrich,12.633) |
| c | 1 | 3 | 2,3,5-CH$_3$ | 2,3,5-trimethyl-4-methoxy-phenol[1] |
| d | 2 | 0 | — | 2,4-dimethoxy-phenol[2] |
| e | 1 | 0 | — | 4-methoxyphenol (Aldrich,M1,865-5) |

[1] Prepared from 4-methoxy-2,3,6-trimethylbenzaldehyde (J. R. Merchant et al., J. Indian Chem. Soc. 40, 472 (1963)) by Baeyer Villiger oxidation (analogously to M. V. Sargent et al., J. Chem. Soc. 1974, p.1353)
[2] R. O. Duthaler et al., Helv. Chim. Acta 67, 1411 (1984)

TABLE 2

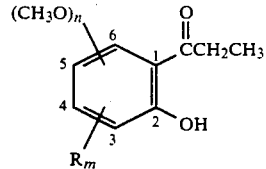

III

| Example | n | CH$_3$O in position | m | R | m.p. °C./ $R_f$ value[1] | Yield % |
|---|---|---|---|---|---|---|
| a | 2 | 4,6- | 0 | — | 113°–116° 0.51 | 67 |
| b | 2 | 3,4- | 0 | — | 0.49, oil | 61 |
| c | 1 | 5- | 3 | 3,4-6-CH$_3$ | 74°–76° | 40 |
| d | 2 | 3,5- | 0 | — | 0.54, oil | 55 |
| e | 1 | 5- | 0 | — | pale oil 0.57 | 45 |

[1] Cyclohexane/ethyl acetate = 4:1

Example 2a (m=0, n=2) R$^2$ and R$^4$=H, R$^3$=F 2-(4-Fluorophenyl)-oxycarbonyl-4,6-dimethoxypropiophenone 4.5 g (0.15 mol) of sodium hydride (80% suspension in oil, Fluka AG) are suspended under argon in 150 ml of absolute tetrahydrofuran in a four-necked flask. A solution of 31.5 g (0.15 mol) of 2-hydroxy-4,6-dimethoxypropiophenone (IIIa) in 350 ml of absolute THF is added slowly dropwise at room temperature. The temperature rises to 40° C. and a blue solution forms. The solution is stirred for a further 1 hour. 23.8 g (0.15 mol; 17.7 ml) of p-fluorobenzoyl chloride (IVa) (R$^2$=H, R$^3$=F, R$^4$=H) in 100 ml of absolute THF are then added dropwise. The batch is decolorized with a slight evolution of heat. The mixture is stirred for a further 1 hour at room temperature. The reaction mixture is concentrated under vacuum and the residue is extracted with ethyl acetate/water. The combined organic extracts are dried over MgSO$_4$, filtered and concentrated under vacuum.

Yield: 60 g, chromatography on silica gel with cyclohexane/ethyl acetate=4:1 gives 49 g of Va, white crystals (95% of theory) m.p. 74° C., $R_f$ value=0.34

Example 2b–2f

Compounds Vb–Vf are prepared in a manner analogous to that described in Example 2a (cf. Tab. 3).

TABLE 3

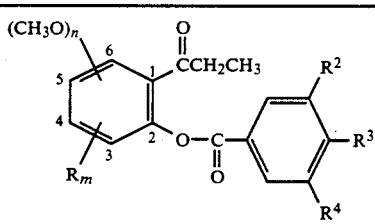

V

| Example | n | CH$_3$O in position | m | R | R$^2$ | R$^3$ | R$^4$ | m.p. °C./ $R_f$ value[1] | Yield % |
|---|---|---|---|---|---|---|---|---|---|
| a | 2 | 4,6- | 0 | — | H | F | H | 74°/0.32[2] | 95 |
| b | 2 | 4,6- | 0 | — | H | OCH$_3$ | H | 82°/0.55[3] | 97 |
| c | 2 | 4,6- | 0 | — | H | Cl | H | 89°–91°/0.34[1] | 89 |
| d | 2 | 4,6- | 0 | — | OCH$_3$ | OCH$_3$ | H | 143°–45°/ | 84 |
| e | 1 | 5- | 3 | 3,4-6-CH$_3$ | H | F | H | 95°–98°/ | 30 |

TABLE 3-continued

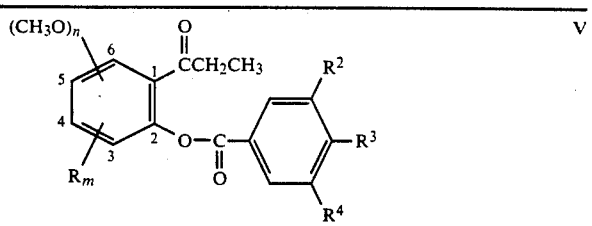

| Example | n | CH3O in position | m | R | R² | R³ | R⁴ | m.p. °C./ Rf value[1] | Yield % |
|---|---|---|---|---|---|---|---|---|---|
| f | 1 | 5- | 0 | — | H | F | H | /0.48[2] | 60 |

[1] Cyclohexane/ethyl acetate = 2:1
[2] Cyclohexane/ethyl acetate = 4:1
[3] Cyclohexane/ethyl acetate = 1:1

Example 3a (m=0, n=2, R² and R⁴=H, R⁶=F)

2-(4'-Fluorophenyl)-3-methyl-5,7-dimethoxy-4H-1-benzopyran-4-one (VIa)

0.7 g (17.4 mmol) of sodium hydride (80% suspension in oil) are suspended in 20 ml of absolute dimethyl sulfoxide at room temperature in a four-necked flask and the suspension is stirred for 30 minutes at room temperature. 1.92 g (5 mmol) of 2-(4-fluorophenyl)-oxycarbonyl-4,6-dimethoxypropiophenone (Va) dissolved in 10 ml of absolute DMSO are then added dropwise under argon. The mixture is stirred for a further 1-2 hours at room temperature. The reaction mixture is then treated at 0° C. with 50 ml of concentrated aqueous oxalic acid solution and stirred for a further 30 min. The batch is extracted with ethyl acetate and the ethyl acetate extracts are dried over MgSO₄, filtered and concentrated under vacuum. The residue is heated with 50 ml of glacial acetic acid 2 ml of concentrated hydrochloric acid for 1-2 hours under reflux and is then concentrated under vacuum. The residue is dissolved in methylene chloride and the solution is washed with cold saturated sodium bicarbonate solution and the CH₂Cl₂ phase is dried over MgSO₄ and concentrated under vacuum.

Yield: 0.91 g white crystals of VIa (58% of theory) m.p. 252°-256° C. Rf value=0.36 (cyclohexane/ethyl acetate=1:1)

Example 3b-3f

Compounds VIa-VIf are prepared in a manner analogous to that described in Example 3a (cf. Tab.4 )

TABLE 4

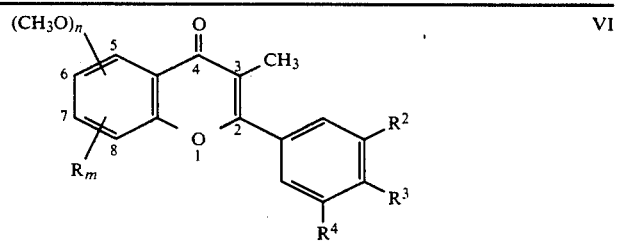

| Example | n | CH3O in position | m | R | R² | R³ | R⁴ | m.p. °C./ Rf value[1] | Yield % |
|---|---|---|---|---|---|---|---|---|---|
| a | 2 | 5,7- | 0 | — | H | F | H | 152-56°/0.36[2] | 58 |
| b | 2 | 5,7- | 0 | — | H | OCH₃ | H | 183-85°/0.49[2] | 48 |
| c | 2 | 5,7- | 0 | — | H | Cl | H | 198-200°/0.10[3] | 62 |
| d | 2 | 5,7- | 0 | — | OCH₃ | OCH₃ | H | 146-70°/0.14[2] | 94 |
| e | 1 | 6- | 3 | 5,7,8-CH₃ | H | F | H | /0.19[2] | 39 |
| f | 1 | 6- | 0 | — | H | F | H | 112°/0.39[1] | 41 |

[1] Cyclohexane/ethyl acetate = 4:1;
[2] Cyclohexane/ethyl acetate = 1.:1;
[3] Cyclohexane/ethyl acetate = 2:1

Example 4a (m=0, n=2, R² and R⁴=H, R³=F)

2-(4'-Fluorophenyl)-3-methyl-5,7-dihydroxy-4H-1-benzopyran-4-one (VIIa)

0.9 g (2.9 mmol) of 2-(4'-fluorophenyl-3-methyl-5,7-dimethoxy-4H-1-benzopyran-4-one (VIa) are heated to 110° C. in 3.5 ml of hydriodic acid (57%) for 1 hour under argon. The reaction mixture is then added to a mixture of 50 ml of H₂O and 50 ml of ethyl acetate. The ethyl acetate phase is separated off and washed once with water and once with saturated sodium bicarbonate solution until acid-free, dried over MgSO₄, filtered and concentrated under vacuum. The product is chromatographed on silica gel using cyclohexane/ethyl acetate=4:1 as the eluent.

Yield: 0.63 g of pale yellow crystals of VIIa (82% of theory) m.p.=276°-279° C. Rf value=0.74 (cyclohexane/ethyl acetate=1:1)

Example 4b-4g

Compounds VIIb-VIIg are prepared in a manner analogous to that described in Example 4a (cf. Tab. 5).

TABLE 5

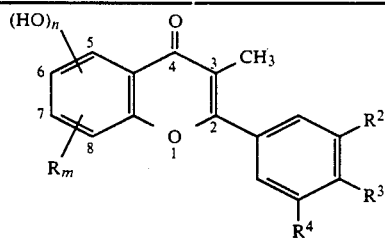

| Example | n | HO in position | m | R | R² | R³ | R⁴ | m.p. °C./ $R_f$ value | Yield % | Molecular mass found MS: m/e |
|---|---|---|---|---|---|---|---|---|---|---|
| a | 2 | 5,7- | 0 | — | H | F | H | 276–79°/0.74[1] | 82 | 286 |
| b | 2 | 5,7- | 0 | — | H | OH | H | 307–09°/0.48[2] | 90 | 284 |
| c | 2 | 5,7- | 0 | — | H | Cl | H | /0.15[4] | 65 | 302 |
| d | 2 | 5,7- | 0 | — | OH | OH | H | /0.1[3] | 72 | 300 |
| e | 1 | 6- | 3 | 5,7,8-CH₃ | H | F | H | /0.51[2] | 53 | 312 |
| f | 1 | 6- | 0 | — | H | F | H | /0.43[2] | 76 | 270 |
| g | 2 | 5,7- | 0 | — | H | OCH₃ | H | /0.53[2] | 78 | 298 |

[1] Cyclohexane/ethyl acetate = 1:1;
[2] Cyclohexane/ethyl acetate = 2:1;
[3] Ethyl acetate/MeOH = 97:3;
[4] Ethyl acetate Example 5a (m=0, n=2, R²′ and R⁴′=H, R³′=F)

2-(4′-Fluorophenyl)-3-methyl-5,7-bisacetoxy-4H-1-benzopyran-4-one (VIIIa)

0.63 g (2.2 mmol) of 2-(4′-fluorophenyl)-3-methyl-5,7-dihydroxy-4H-1-benzopyran-4-one VIIa are dissolved in 8 ml of acetic anhydride with the exclusion of moisture. After adding 1.5 ml of absolute pyridine, the mixture is heated at 100° C. for 2 hours. The reaction mixture is then treated and extracted with a 1:1 mixture of 50 ml of ethyl acetate/ice water. The aqueous phase is extracted twice more with ethyl acetate. The combined organic extracts are dried over MgSO₄, filtered and concentrated under vacuum. The product is chromatographed on 60 μm silica gel (Merck AG, Darmstadt) using cyclohexane/ethyl acetate=4:1 as the eluent.

Yield: 0.81 g of pale crystals of VIIIa (98% of theory) m.p.=147°–149° C. $R_f$ value=0.35 (cyclohexane/ethyl acetate=1:1)

Example 5b–5g

Compounds VIIIa–VIIIg are prepared in a manner analogous to that described in Example 5a (cf Tab. 6).

TABLE 6

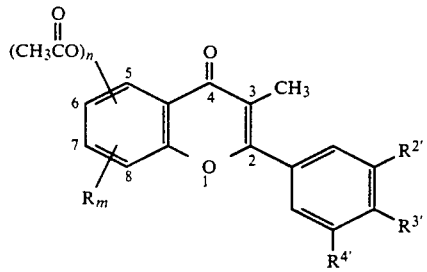

| Example | n | CH₃C—O in position | m | R | R²′ | R³′ | R⁴′ | m.p. °C./ $R_f$ value | Yield % | Molecular mass found MS: m/e |
|---|---|---|---|---|---|---|---|---|---|---|
| a | 2 | 5,7- | 0 | — | H | F | H | 147–49°/0.35[1] | 98 | 370 |
| b | 2 | 5,7- | 0 | — | H | OAc* | H | 146–50°/0.4[2] | 73 | 410 |
| c | 2 | 5,7- | 0 | — | H | Cl | H | /0.29[1] | 62 | 386 |
| d | 2 | 5,7- | 0 | — | OAc* | OAc* | H | /204–06° 0.49[2] | 78 | 486 |
| e | 1 | 6- | 3 | 5,7,8-CH₃ | H | F | H | /0.42[2] | 82 | 354 |
| f | 1 | 6- | 0 | — | H | F | H | /0.38[1] | 86 | 312 |
| g | 2 | 5,7- | 0 | — | H | OCH₃ | H | /0.34[1] | 92 | 340 |

[1] Cyclohexane/ethyl acetate = 4:1;
[2] Cyclohexane/ethyl acetate = 1:1;
*Ac = acetyl Example 6a (m=0, n=2, R²′ and R⁴′=H, R³′=F, Hal=bromine, AC=acetyl)

2-(4′-Fluorophenyl)-3-bromomethyl-5,7-bisacetoxy-4H-1-benzopyran-4-one (IXa)

2.8 g (7.4 mmol) of 2-(4′-fluorophenyl)-3-methyl-5,7-bis-acetoxy-4H-1-benzopyran-4-one (VIIIa) are dissolved in 50 ml of absolute carbon tetrachloride. After adding 0.88 g (4.8 mmol) of N-bromosuccinimide and 0.1 g of N,N-azo-bis-(isobutyronitrile), the mixture is heated under reflux for 3–4 hours with the exclusion of moisture. After adding a further 0.44 g (2.4 mmol) of N-bromosuccinimide, the mixture is boiled under reflux for 4 hours. After cooling, the succinimide which has precipitated is filtered off. The filtrate is concentrated and the residue is recrystallized from ethyl acetate.

Yield: 2.5 g of white crystals of IXa (76% of theory) m.p. 167°–170° C. $R_f$ value: 0.64 (toluene/ethyl acetate=4:1)

Example 6b–6g

Compounds IXb–IXg are prepared in a manner analogous to that described in Example 6a (cf. Tab. 7).

under vacuum. The resulting phytyl bromide ($R^1$-Br) (11.0 g; 92.8% of theory) is further reacted direct.

B) 2.5 g (33 mmol) of thiourea are dissolved in 25 ml of absolute ethanol. 11.0 g (30.5 mmol) of phytyl bromide ($R^1$-Br) from batch A) dissolved in 25 ml of absolute ethanol are added to the solution. The mixture is heated under reflux for 6 hours. On cooling, the isothiuronium salt formed precipitates out. The salt can be filtered off with suction or is further processed direct. For this purpose, 10 ml of 5N sodium hydroxide solution are added to the batch and the mixture is heated under reflux for 2 hours. After cooling, the pH is adjusted to 4 with 2N hydrochloric acid and the mercaptan is extracted three times with diethyl ether (50 ml

TABLE 7

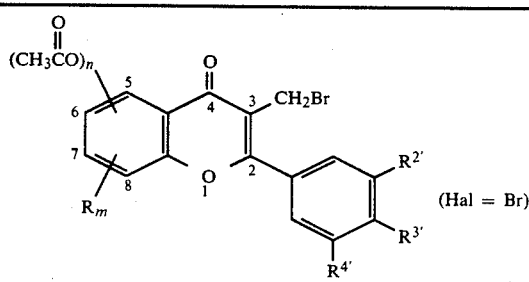

(Hal = Br)                                                                                              IX

| Example | n | CH$_3$C(=O)—O in position | m | R | R$^{2'}$ | R$^{3'}$ | R$^{4'}$ | m.p. °C./ $R_f$ value | Yield % | Molecular mass found MS: m/e |
|---|---|---|---|---|---|---|---|---|---|---|
| a | 2 | 5,7- | 0 | — | H | F | H | 167–70°/ 0.64[1] | 76 | 449 |
| b | 2 | 5,7- | 0 | — | H | OAc* | H | 157–59°/ 0.48[1] | 85 | 489 |
| c | 2 | 5,7- | 0 | — | H | Cl | H | /0.46[2] | 93 | 465 |
| d | 2 | 5,7- | 0 | — | OAc* | OAc* | H | /148–52°/ 0.42[1] | 95 | 547 |
| e | 1 | 6- | 3 | 5,7,8-CH$_3$ | H | F | H | /0.59[1] | 56 | 432 |
| f | 1 | 6- | 0 | — | H | F | H | /0.45[1] | 82 | 390 |
| g | 2 | 5,7- | 0 | — | H | OCH$_3$ | H | 101–105°/ 0.51[1] | 95 | 418 |

[1] Toluene/ethyl acetate = 4:1;
[2] Cyclohexane/ethyl acetate = 2:1;
*Ac = acetyl

Example 7a ($R^1$=phytyl, X=S)

3,7R,11R,15-Tetramethyl-2E-hexadecenyl mercaptan (Xa)

A) 9.5 g (33 mmol) of 3,7R,11R,15-tetramethyl-2E-hexadecen-1-ol (phytol, Aldrich 13, 991-2) are dissolved in 30 ml of absolute methylene chloride. 2.1 ml of phosphorus tribromide are added dropwise at 0° C. The mixture is then stirred for a further 3 hours at 0° C. The reaction batch is added to 50 ml of ice-water and extracted with methylene chloride. The methylene chloride extracts are washed acid-free with dilute NaHCO$_3$ solution, dried over MgSO$_4$, filtered and concentrated each time). The ether extracts are dried over MgSO$_4$, filtered and concentrated under vacuum. Chromatography on Merck 60 μm silica gel with cyclohexane/ethyl acetate 10:1 gives Xa.

Yield: 5.9 g of pale oil Xa (58% of theory) $R_f$ value=0.73 (cyclohexane/ethyl acetate=4:1)

Example 7b–7f, 7h, 7i

Compounds Xb–Xf, Xh and Xi are prepared from the commercially available alcohols in a manner analogous to that described in Example 7a (cf. Tab. 8).

Example 7g

Xg is obtained by the addition of ethanol to Xe.

TABLE 8

| | $R^1$—S—H    X (X = S) | | |
|---|---|---|---|
| $R^1$ | $R_f$ Value | Yield[1] % | Molecular mass found MS: m/e |
| a  phytyl | 0.73[2] | 58 | 312 |

TABLE 8-continued

R¹—S—H    X (X = S)

| R¹ | | $R_f$-Value | Yield[1] % | Molecular mass found MS: m/e |
|---|---|---|---|---|
| b | retinyl | 0.75[2] | 39 | 302 |
| c | farnesyl | 0.58[2] | 40 | 238 |
| d | geranyl | 0.49[2] | 61 | 170 |
| e | neryl | 0.51[2] | 65 | 170 |
| f | 2-methyl-2-butenyl | 0.48[2] | 70 | 102 |
| g | | 0.55[3] | 34 | 230 |
| h | | 0.58[4] | 42 | 104 |
| i | | 0.52[4] | 55 | 174 |

[1] Yield after chromatography, based on the alcohol (R¹—OH) employed
[2] Cyclohexane/ethyl acetate = 4:1
[3] Cyclohexane/ethyl acetate = 2:1
[4] Cyclohexane Example 8a (m=0, n=2, R²′ and R⁴′=H, R³′=F, X=S)

2-(4′-Fluorophenyl)-3-(2-thia-octadecyl)-5,7-bisacetoxy-4H-1-benzop-Yran-4-one (XIa)

0.9 g (2 mmol) of 2-(4′-fluorophenyl)-3-bromomethyl-5,7-bisacetoxy-4H-1-benzopyran-4-one (IXa) in 20 ml of absolute tetrahydrofuran are added to a suspension of sodium cetyl mercaptan (prepared from 0.62 g (2.5 mmol) of cetyl mercaptan (Aldrich H 763-7) and 0.11 g (2.5 mmol) of sodium hydride (55% suspension in oil) in 20 ml of absolute tetrahydrofuran) at room temperature. The mixture is stirred for about 3 hours under argon. The reaction batch is then treated and extracted with 50 ml of ethyl acetate and 50 ml of water. The organic extracts are dried over MgSO₄, filtered and concentrated under vacuum. The residue is chromatographed on Merck 60 μm silica gel using cyclohexane/ethyl acetate=8:2.

Yield: 1.05 g of yellow crystals of XIa (83% of theory) MS: molecular mass found 626 $R_f$ value: 0.95 (cyclohexane/ethyl acetate=2:1)

Example 8b–8y

Compounds XIb–XIy are prepared in a manner analogous to that described in Example 8a. For all examples in which X=oxygen, the corresponding commercially available alcohols R¹-OH are employed in place of the mercaptans R¹-SH, but in other respects the reaction is as described under Example 8a (cf. Tab. 9).

TABLE 9

XI (structure shown: chromone-type with (CH₃CO)ₙ, positions 5,6,7,8, R₁-CH₂-X linkage at position 3, aryl with R²', R³', R⁴' at position 2, Rₘ substituent)

| Ex. | R¹ | X | n | CH₃C(O)—O in position | m | R | R²' | R³' | R⁴' | Rf value | Yield % | Molecular mass found MS: m/e |
|---|---|---|---|---|---|---|---|---|---|---|---|---|
| a | n-C₁₆H₃₃ | S | 2 | 5,7- | 0 | — | H | F | H | 0.9[1] | 72 | 626 |
| b | n-C₁₂H₂₅ | S | 2 | 5,7- | 0 | — | H | F | H | 0.70[1] | 92 | 570 |
| c | CH₃ | O | 2 | 5,7- | 0 | — | H | F | H | 0.92[2] | 80 | 400 |
| d | n-C₁₈H₃₇ | S | 2 | 5,7- | 0 | — | H | F | H | 0.85[1] | 98 | 654 |
| e | (Phytyl, E) | S | 2 | 5,7- | | | H | F | H | 0.95[1] | 72 | 680 |
| f | n-C₁₂H₂₅ | S | 2 | 5,7- | 0 | — | H | OAc* | H | 0.78[1] | 84 | 610 |
| g | n-C₁₆H₃₃ | S | 2 | 5,7- | 0 | — | H | OAc* | H | 0.8[1] | 78 | 666 |
| h | n-C₁₈H₃₇ | S | 2 | 5,7- | 0 | — | H | OAc* | H | 0.75[1] | 63 | 694 |
| i | (Phytyl, E) | S | 2 | 5,7- | 0 | — | H | OAc* | H | 0.65[1] | 82 | 720 |
| j | (saturated phytyl) | S | 2 | 5,7- | 0 | — | H | OCH₃ | H | 0.70[1] | 59 | 598 |

[1] Cyclohexane/ethyl acetate = 2:1;
[2] Methylene chloride/methanol = 10:1

[1] Toluene/ethyl acetate = 4:1;
*Ac = acetyl

TABLE 9-continued
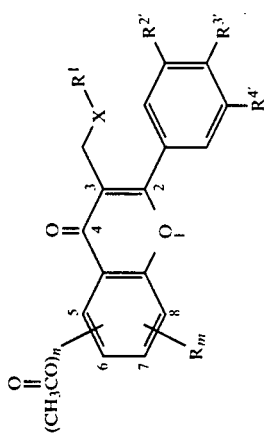
| Ex. | R¹ | X | n | CH₃C(O)—O in position | m | R | R² | R³' | R⁴' | R_f value | Yield % | Molecular mass found |
|---|---|---|---|---|---|---|---|---|---|---|---|---|
| k | (isopentyl) | S | 2 | 5,7- | 0 | — | H | OCH₃ | H | 0.69[1] | 77 | 529 |
| l | (Farnesyl, E,E) | S | 2 | 5,7- | 0 | — | H | F | H | 0.71[1] | 93 | 606 |
| m | (Farnesyl, E,E) | S | 2 | 5,7- | 0 | — | H | OCH₃ | H | 0.50[1] | 87 | 618 |
| n | (ethoxy Z-alkenyl) | S | 2 | 5,7- | 0 | — | H | F | H | 0.82[1] | 69 | 584 |
| o | (ethoxy Z-alkenyl) | S | 2 | 5,7- | 0 | — | H | OCH₃ | H | 0.44[1] | 52 | 596 |
| p | (E-alkenyl) | S | 1 | 6- | 3 | 5,7,8-CH₃ | H | F | H | 0.73[4] | 63 | 590 |
[1] Cyclohexane/ethyl acetate = 2:1;

TABLE 9-continued

XI

[Structure: chromone-type compound with (CH₃CO–O)ₙ substituents at positions 5,6,7,8 on ring, carbonyl at position 4, O at position 1, and CH₂–X–R¹ substituent; attached phenyl with R²', R³', R⁴']

| Ex. | R¹ | X | n | CH₃C(=O)–O in position | m | R | R²' | R³' | R⁴' | $R_f$ value | Yield % | Molecular mass found |
|---|---|---|---|---|---|---|---|---|---|---|---|---|
| q | [prenyl/geranyl-type chain, E] | S | 1 | 6- | 0 | — | H | F | H | 0.68[4] | 72 | 423 |
| r[1] | [chain with Z config] | S | 2 | 7,8- | 0 | — | H | F | H | 0.64[4] | 48 | 423 |
| s | [longer polyene chain, E,E,E] | S | 2 | 5,7- | 0 | — | H | F | H | 0.92[3] | 39 | 671 |
| t[2] | [cyclohexenyl polyene chain, E] | S | 2 | 6,8- | 0 | — | H | F | H | 0.88[3] | 78 | 680 |
|  |  |  |  |  |  |  |  |  |  | MS: m/e/MNR δ-values CDCl₃ |  |  |
| u | [chain, E] | S | 2 | 5,7- | 0 | — | H | F | H | 0.71[1] | 70 | 538 |

[1] Prepared from Example 1b (IIIb) in a manner analogous to that described for Example 9a (Ia)
[2] Prepared from Example 1d (IIId) in a manner analogous to that described for Example 9a (Ia)
[3] Cyclohexane/ethyl acetate = 2:1
[4] Cyclohexane/ethyl acetate = 4:1

TABLE 9-continued
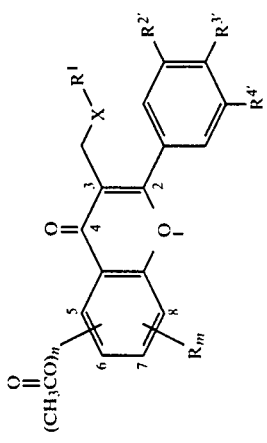
| Ex. | R¹ | X | n | CH₃C(=O)—O in position | m | R | R² | R³ | R⁴ | Rf value | Yield % | Molecular mass found |
|---|---|---|---|---|---|---|---|---|---|---|---|---|
| v | | S | 2 | 5,7- | 0 | — | H | F | H | 0.70[1] | 83 | 538 |
| w | n-C₈H₁₇ | S | 2 | 5,7- | 0 | — | H | F | H | 0.69[1] | 62 | 514 |
| x | n-C₄H₉ | S | 2 | 5,7- | 0 | — | H | F | H | 0.61[1] | 49 | 458 |
| y | | S | 2 | 5,7- | 0 | — | H | OH | OH | 0.60[2] | 50 | 778/0.9(d, 12H, CH₃), 1.0–1.7(m, 19H, CH₂, CH), 1.72(s, 3H, CH₃), 2.0(t, 2H, CH₂), 2.32(s, 6H, OAc), 2.50(s, 3H, OAc), 2.75 (s, 3H, OAc), 3.35(d, 2H, SCH₂), 3.68(s, 2H, SCH₂), 5.32(t, 1H, J=8Hz, CH=), 6.9–8.0(5H, aromatic protons) |
[1]Cyclohexane/ethyl acetate = 2:1;
[2]Cyclohexane/ethyl acetate 1:1

Example 9a (m=0, n=2, $R^2$ and $R^4$=H, $R^3$=F, X=S)

2-(4'-Fluorophenyl)-3-(2-thia-octadecyl)-5,7-dihydroxy-4-H-1-benzopyran-4-one Ia 0.8 g (1.3 mmol) of 2-(4'-fluorophenyl)-3-(2-thiaoctadecyl)-5,7-bisacetoxy-4H-1-benzopyran-4-one (XIa) are dissolved in 10 ml of methanol After adding 0.37 g (27 mmol) of powdered potassium carbonate, the mixture is stirred for 2 hours at room temperature. The reaction batch is treated and extracted with 30 ml of ethyl acetate and 40 ml of water. The organic extracts are dried over $MgSO_4$, filtered off and concentrated under vacuum.

Yield: 0.6 g of pale crystals (86% of theory) of Ia MS: molecular mass found 542 $R_f$ value: 0.61 (cyclohexane/ethyl acetate=2:1) m.p.: 110°–112° C.

Examples 9b–9y

Compounds Ib–Iy are prepared in a manner analogous to that described in Example 9a (cf. Tab. 10).

TABLE 10

[Structure: chromone with (HO)_n on benzopyran ring (positions 5,6,7,8), R_m substituent, C=O at 4, at position 3 a CH2-X-R^1 group, at position 2 a phenyl ring bearing R^2, R^3, R^4]

[Phytyl group structure shown]

| Ex. | R^1 | X | n | OH in position | m | R | R^2 | R^3 | R^4 | m.p. °C./ R_f value | Yield % | MS/NMR δ-values in CDCl_3 |
|---|---|---|---|---|---|---|---|---|---|---|---|---|
| a | n-C_16H_33 | S | 2 | 5,7- | 0 | — | H | F | H | 110–112°/0.57[1] | 95 | 542/0.9(t, 3H, CH_3), 1.2(broad s, 28H, CH_2), 2.7(t, 2H, SCH_2), 3.6(s, 2H, SCH_2), 6.2–6.4(m, 2H, aromat.H), 7.1–7.5 and 7.6–8.0(m, 4H, aromat.H) |
| b | n-CH_12H_25 | S | 2 | 5,7- | 0 | — | H | F | H | 109°/0.57[2] | 79 | 486/0.9(t, 3H, CH_3), 1.2(broad s, 20H, CH_2), 2.65(t, 2H, SCH_2), 3.6(s, 2H, SCH_2), 5.8(broad s, 1H, OH), 6.2–6.5(m, 2H), 7.1–7.4(m, 2H), 7.6–8.0(m, 2H, aromat.prot.), 13.0(s, 1H, OH) |
| c | CH_3 | O | 2 | 5,7- | 0 | — | H | F | H | 250°  0.75[2] | 72 | 316/2.2(s, 2H, OH), 3.4(s, 3H, OCH_3), 4.2(s, 2H, SCH_2), 6.25(dd, 2H), 7.15(t, 2H), 7.8(m, 2H, aromat.H) |
| d | C_18H_37 | S | 2 | 5,7- | 0 | — | H | F | H | 119–120°  0.45[1] | 84 | 570/0.9(t, 3H, CH_3), 1.25(broad s, 32H, CH_2), 2.70(t, 2H, J = 6Hz, SCH_2), 3.65(s, 2H, SCH_2), 6.1(broad s, 1H, OH), 6.2–6.4(m, 2H), 7.3(t, 2H), 7.7–8.0(m, 2H, aromat.prot.), 13.2(s, 1H, OH) |
| e | (Phytyl) | S | 2 | 5,7- | 0 | — | H | F | H | 50–54°  0.61[1] | 93 | 596/0.8–0.9(12H, CH_3), 1.0–1.7(m, 19H, CH_2, u.CH), 1.94(t, CH_2, 2H), 3.34(d, J = 8Hz, 2H, SCH_2), 5.24 (t, J = 8Hz, —CH=, 1H), 6.3(dd, 2H), 7.2(t, 2H), 7.75–7.9(m, 2H, aromat.prot), 5.9(broad s, 1H, OH), 12.8(s, 1H, OH), 1.62 (s, 3H, CH_3) |
| f | n-C_12H_25 | S | 2 | 5,7- | 0 | — | H | OH | H | 133°/ | 89 | 484/(DMSO)*; 0.9(t, 3H, CH_3), 1.2(broad s, 18H, CH_2), 2.4–2.6(DMSO), 3.6(s, 2H, CH_2S), 3.3(broad s, H_2O, 1H), 6.3(dd, 2H), 7.0(d, 2H), 7.6–7.8(m, 2H, aromat.H) 13(s, 1H, OH) |
| g | n-C_16H_33 | S | 2 | 5,7- | 0 | — | H | OH | H | 136°/0.21[1] | 94 | 540/0.9(t, 3H, CH_3), 1.26(broad s, 28H, CH_2), 2.65(t, 2H, SCH_2), 3.66(s, 2H, SCH_2), 5.6(s, 1H, OH), 6.3(dd, 2H), 7.7(d, 2H, aromat.prot.) 12.7(s, 1H, OH) |
| h | n-C_18H_37 | S | 2 | 5,7- | 0 | — | H | OH | H | 136°/0.21[1] | 72 | 568/(DMSO)*; 0.9(t, 3H, CH_3), 1.2(broad s, 32H, CH_2), 2.4–2.6(DMSO, SCH_2), 3.3(broad |

[1])Cyclohexane/ethyl acetate = 2:1;
[2])Methylene chloride/MeOH = 10:1

[1])Cyclohexane/ethyl acetate = 2:1

[1])Toluene/ethyl acetate = 4:1;
*)in DMSO instead of in CDCl_3

TABLE 10-continued

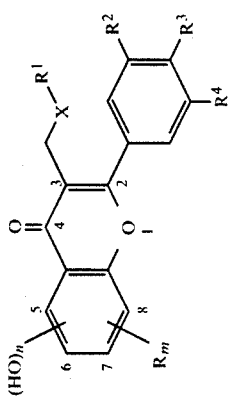

| Ex. | R¹ | X | n | OH in position | m | R | R² | R³ | R⁴ | m.p. °C./R_f value | Yield % | |
|---|---|---|---|---|---|---|---|---|---|---|---|---|
| i | (Phytyl) | S | 2 | 5,7- | 0 | — | H | OH | H | amorphous powder 0.18[1] | 84 | 594/0.8–0.9(d, 12H, CH₃), 1.0–1.7(m, 19H, CH₂, CH), 1.95(t, J=8Hz, 2H, CH₂), 3.36(d, J=8Hz, 2H; SCH₂), 3.62(s, 2H, SCH₂), 5.26(t, J=8Hz, CH=, 1H), 6.3(dd, 2H), 6.96(d, 2H), 7.7–7.8(m, 2H, aromat.H), 12.9(s, 1H, OH), 1.63(s, 3H, CH₃) s, H₂O), 3.60(s, 2H, SCH₂), 6.3(dd, 2H), 7.0(d, 2H), 7.7(m, 2H, aromat.H) 13(s, 2H, OH) |
| j | | S | 2 | 5,7- | 0 | — | H | OCH₃ | H | /0.2[1] | 69 | 514/ |
| k | | S | 2 | 5,7- | 0 | — | H | OCH₃ | H | /0.51[2] | 63 | 445/ |
| l | (Farnesyl) | S | 2 | 5,7- | 0 | — | H | F | H | 50°/0.54[2] | 88 | 522/1.55–1.73(12H, CH₃), 1.9–2.15(m, 7H, CH₂), 2.68(t, 1H, CH₂), 3.35(d, 2H, SCH₂), 3.58(s, 2H, SCH₂), 5.02–5.15(m, 2H, CH=), 5.25(t, 1H, CH=), 7.72(s, 1H, OH), 6.3(dd, 2H), 7.22(t, 2H), 7.8–7.9(m, 2H, aromat.H), 12.8(s, 1H, OH) |
| m | (Farnesyl) | S | 2 | 5,7- | 0 | — | H | OCH₃ | H | 139° 0.52[1] | 81 | 534/1.57–1.72(12H, CH₃), 1.9–2.15(m, 7H, CH₂), 2.69(t, 1H, CH₂), 3.35(d, 2H, SCH₂), 3.63(s, 2H, SCH₂), 3.68(s, 3H, OCH₃), 5.05–5.15(m, 2H, CH=), 5.28(t, 1H, CH=), 5.38(s, 1H, OH), 6.48(q, 2H), 6.97(d, 2H), 7.78(d, 2H, aromat.H), 12.85(s, 1H, OH) |

[1] Toluene/ethyl acetate = 4:1;
*) in DMSO instead of in CDCl₃

[1] Toluene/ethyl acetate = 4:1;
[2] Cyclohexane/ethyl acetate = 2:1

[1] Cyclohexane/ethyl acetate = 2:1

TABLE 10-continued

| Ex. | R¹ | X | n | OH in position | m | R | R² | R³ | R⁴ | m.p. °C./ R_f value | Yield % | |
|---|---|---|---|---|---|---|---|---|---|---|---|---|
| n | | S | 2 | 5,7- | 0 | — | H | F | H | viscous oil 0.64[1] | 63 | 500/1.1–1.2(6H, CH₃), 1.38–1.45(m, 4H, CH₂), 1.70(m, 3H, CH₃), 1.9–2.1(m, 2H, CH₂), 3.32 (d, 2H, SCH₂), 3.37(q, 2H, OCH₂), 3.58 (s, 2H, SCH₂), 5.26(t, 1H, CH=), 6.3(dd, 2H), 6.6(broad s, 1H, OH), 7.22(t, 2H), 7.75–7.90 (m, 2H, aromat.H), 12.8(s, 1H, OH) |
| o | | S | 2 | 5,7- | 0 | — | H | OCH₃ | H | 0.47[1] | 55 | 512/cf.Ex.9n, 3.22(d, 2H, SCH₂), 3.41(q, 2H, OCH₂), 3.62(s, 2H, SCH₂), 3.86(s, 3H, OCH₃), 5.25(t, 1H, CH=), 6.37(dd, 2H), 6.45(broad s, OH), 6.96(d, 2H), 7.7(d, 2H, aromat.H), 12.85(s, OH) |

[1] Cyclohexane/ethyl acetate = 2:1

| Ex. | R¹ | X | n | OH in position | m | R | R² | R³ | R⁴ | m.p. °C./ R_f value | Yield % | Molecular mass fond M = m/e |
|---|---|---|---|---|---|---|---|---|---|---|---|---|
| p | | S | 1 | 6- | 3 | 5,7,8-CH₃ | H | F | H | /0.52[4] | 81 | 548 |
| q | | S | 1 | 6- | 0 | — | H | F | H | /0.91[3] | 63 | 438 |
| r[1] | | S | 2 | 7,8- | 0 | — | H | F | H | /0.73[3] | 49 | 454 |
| s | | S | 2 | 5,7- | 0 | — | H | F | H | /0.62[3] | 28 | 587 |

TABLE 10-continued

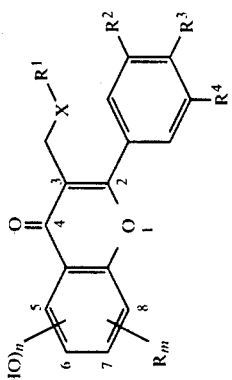

| Ex. | R¹ | X | n | OH in position | m | R | R² | R³ | R⁴ | m.p. °C./ $R_f$ value | Yield % | MS/NMR δ-values in CDCl₃ |
|---|---|---|---|---|---|---|---|---|---|---|---|---|
| t[2] | 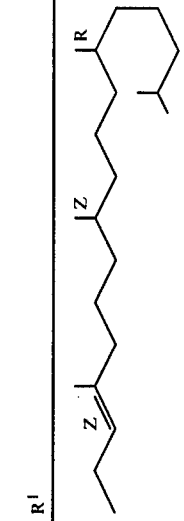 | S | 2 | 6,8- | 0 | — | H | F | H | /0.63[3] | 70 | 596 |
| u | (structure) | S | 2 | 5,7- | 0 | — | H | F | H | 152°/0.58[1] | 58 | 454/1.58(s, 3H, CH₃), 1.66(s, 6H, CH₃), 1.9-2.1(m, 4H, CH₂), 3.34(d, 2H, SCH₂), 3.58(s, 2H, SCH₂), 5.05(t, 1H, CH=), 5.26(t, 1H, CH=), 5.95(bs, 1H, OH), 6.3(d, 2H), 7.2(t, 2H), 7.8-7.9(m, 2H, aromat.prot.), 12.8(s, 1H, OH) |
| v | (structure) | S | 2 | 5,7- | 0 | — | H | F | H | 83°/0.55[1] | 62 | 454/1.58(s, 3H, CH₃), 1.66(s, 3H, CH₃), 1.71 (s, 3H, CH₃), 1.9-2.1(m, 4H, CH₂), 3.32(d, 2H, CH₂), 3.58(s, 2H, SCH₂), 5.05(t, CH=), 5.26(t, 1H, CH=), 5.5(dd, CH=), 6.3(d, 2H), 7.2(t, 2H), 6.0(bs, 1H, OH), 7.8-7.9(m, 2H, aromat.Prot.), 12.8(s, 1H, CH) |
| w[1] | n-C₈H₁₇ | S | 2 | 5,7- | 0 | — | H | F | H | 124°/0.63[1] | 70 | 430/0.9(t, 3H, CH₃), 1.20-1.40(m, 10H, CH₂), 1.58(p, 2H, CH₂), 2.65(t, 2H, SCH₂), 3.52(s, 2H, SCH₂), 5.93(bs, OH), 6.32(dd, 2H), 7.22(t, 2H), 7.8-7.9(m, 2H, aromat.H), 12.8(s, OH) |
| x | n-C₄H₉ | S | 2 | 5,7- | 0 | — | H | F | H | /0.60[1] | 59 | 374/ |
| y | (structure) | | 2 | 5,7- | 0 | — | H | OH | OH | 0.32[1] | 36 | 610/ |

[1]Prepared from Example 1b (IIIb) in a manner analogous to that described for Example 9a (Ia)
[2]Prepared from Example 1d (IIId) in a manner analogous to that described for Example 9a (Ia)
[3]Cyclohexane/ethyl acetate = 2:1
[4]Cyclohexane/ethyl acetate = 4:1

[1]Cyclohexane/ethyl acetate = 2:1

[1]Cyclohexane/ethyl acetate = 2:1

We claim:
1. A substituted 3-thia- or 3-oxa-alkylflavone of formula I

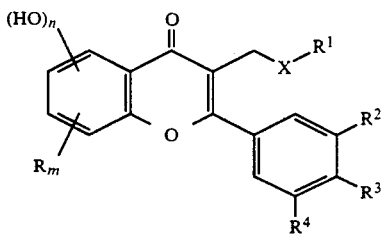

in which:
X is sulfur or oxygen,
R is halogen, $(C_1-C_4)$-alkyl or trifluoromethyl,
m is 0, 1, 2 or 3,
n is 1, or if m=0, 1 or 2, also 2,
$R^1$ is $(C_1-C_{25})$-alkyl or $(C_3-C_{25})$-alkenyl, one $CH_2$ group optionally being replaced by oxygen, or is $(C_3-C_{25})$-alkenyl, which is substituted by cyclohexenyl, which in turn contains 1-3 methyl groups, and
$R^2$, $R^3$ and $R^4$ are hydrogen, hydroxyl, halogen, $(C_1-C_4)$-alkyl, $(C_1-C_4)$-alkoxy or trifluoromethyl, $R^2$, $R^3$ and $R^4$ being identical or different.

2. A compound as claimed in claim 1, wherein, in formula I,
X is sulfur or oxygen,
R is fluorine, chlorine, $(C_1-C_3)$-alkyl or trifluoromethyl,
m is 0, 1, 2 or 3,
n is 1 or, if m is 0, 1 or 2, also 2,
$R^1$ is $(C_4-C_{22})$-alkyl or $(C_4-C_{22})$-alkenyl, wherein one $CH_2$ group may be replaced by oxygen, and
$R^2$, $R^3$ and $R^4$ are hydrogen, hydroxyl, fluorine, chlorine, $(C_1-C_3)$-alkyl, $(C_1-C_3)$-alkoxy or trifluoromethyl, $R^2$, $R^3$ and $R^4$ being identical or different.

3. A compound as claimed in claim 1, wherein, in formula I,
X is sulfur,
R is fluorine, chlorine, methyl or trifluoromethyl,
m is 0, 1, 2 or 3,
n is 1 or, if m is 0, 1 or 2, also 2,
$R^1$ is $(C_4-C_{22})$-alkyl or $(C_4-C_{22})$-alkenyl, wherein one $CH_2$ group may be replaced by oxygen, and
$R^2$, $R^3$ and $R^4$ are hydrogen, hydroxyl, fluorine, chlorine, methyl, methoxy or trifluoromethyl, $R^2$, $R^3$ and $R^4$ being identical or different.

4. A pharmaceutical preparation, containing a pharmaceutically effective amount of a compound as claimed in claim 1 and a pharmaceutically acceptable carrier.

5. A method of treating arteriosclerosis or hypercholesterolemia comprising administering a prophylactic or therapeutic amount of a compound as claimed in claim 1.

* * * * *